United States Patent [19]

Erdmann et al.

[11] Patent Number: 5,099,044
[45] Date of Patent: Mar. 24, 1992

[54] ORGANOMETALLIC COMPOUNDS

[75] Inventors: Dietrich Erdmann, Mühltal-Traisa; Ludwig Pohl; Martin Hostalek, both of Darmstadt, all of Fed. Rep. of Germany

[73] Assignee: Merck Patent Gesellschaft Mit Beschrankter Haftung, Darmstadt, Fed. Rep. of Germany

[21] Appl. No.: 548,872
[22] PCT Filed: Nov. 27, 1989
[86] PCT No.: PCT/EP89/01431
§ 371 Date: Jul. 16, 1990
§ 102(e) Date: Jul. 16, 1990
[87] PCT Pub. No.: WO90/06315
PCT Pub. Date: Jun. 14, 1990

[30] Foreign Application Priority Data

Dec. 10, 1988 [DE] Fed. Rep. of Germany ....... 3841643

[51] Int. Cl.$^5$ .............................. C07F 5/00; C07F 9/02
[52] U.S. Cl. .......................................... 556/1; 556/13; 556/20; 556/70; 556/174
[58] Field of Search .................. 556/13, 20, 70, 1, 174, 556/186, 190

[56] References Cited

FOREIGN PATENT DOCUMENTS 0342444 11/1989 European Pat. Off. ................ 556/1
3631469 3/1988 Fed. Rep. of Germany ...... 556/174

OTHER PUBLICATIONS

Chemical Abstracts, vol. 69, No. 7, 12 Aug. 1968, Abs. No. 27472s, Hubert Schmidbaur et al., "Preparative and spectroscopic studies of dialkylgallium fluorides".
Chemical Abstracts, vol. 68, No. 10, 4 Mar. 1988, Abs. No. 44331s, J. Weidlein et al., "Vibrational spectra of dimethyl-and diethylaluminum fluoride".

Primary Examiner—Jose G. Dees
Assistant Examiner—Porfirio Nazario
Attorney, Agent, or Firm—Millen, White & Zelano

[57] ABSTRACT

The invention relates to organometallic compounds which are intramolecularly stabilized, and also to their use for the production of thin films and epitaxial layers by gas-phase deposition.

7 Claims, No Drawings

ORGANOMETALLIC COMPOUNDS

The invention relates to organometallic compounds which contain aluminum, gallium or indium as metals, and also to the use of said compounds for the production of thin films or epitaxial layers by gas-phase deposition.

The deposition of such layers either from pure elements of the third group or from III-V combinations with other elements, such as for example gallium arsenide, indium phosphide or gallium phosphide, can be used to produce electronic and opto-electronic circuit elements, compound semiconductors and lasers. The deposition of said layers takes place from the gas phase.

The properties of these films depend on the deposition conditions and the chemical composition of the film deposited.

All the known methods such as the Metal-Organic Chemical Vapor Deposition (MOCVD) method, the Photo-Metal-Organic Vapor Phase (Photo-MOVP) method in which the substances are decomposed by UV irradiation, the Laser Chemical Vapor Deposition (Laser CVD) method or the Metal-Organic Magnetron Scattering (MOMS) method, are suitable for deposition from the gas phase. The advantages over other methods are a controllable layer growth, a precise doping control and also simple handling and production-friendliness owing to the normal-pressure or low-pressure conditions.

In the MOCVD method, organometallic compounds are used which decompose to deposit the metal at a temperature below 1100° C. Typical apparatuses which are currently used for MOCVD comprise a "bubbler" having a feed for the organometallic component, a reaction chamber which contains the substrate to be coated, and also a source of a carrier gas, which should be inert toward the organometallic component. The "bubbler" is kept at a constant, relatively low temperature which is preferably above the melting point of the organometallic compound, but far below the decomposition temperature. The reaction chamber or decomposition chamber is preferably at a very much higher temperature which is below 1100° C., at which temperature the organometallic compound completely decomposes and the metal is deposited. The organometallic compound is converted to the vapor state by the carrier gas and is passed through a lock into the decomposition chamber with the carrier gas. The mass flow rate of the vapor can readily be controlled and a controlled growth of the thin layers is consequently also possible.

Hitherto, metal alkyls such as, for example, trimethylgallium, trimethylaluminum or trimethylindium have mainly been used for gas-phase deposition. These compounds are, however, extremely sensitive to air, spontaneously ignitable and partially decomposable even at room temperature. Elaborate safety measures are therefore necessary for the production, the transportation, the storage and the application of these compounds. A few, somewhat more stable adducts of the metal alkyls with Lewis bases such as, for example, trimethylamine and triphenylphosphine are also known (described, for example, in GB 2,123,422, EP-A 108,469 or EP-A 176,537), but these are only suitable to a limited extent for gas-phase deposition owing to the low vapor pressure.

It was therefore the object of the present invention to find metal alkyl compounds which are simple to handle and are stable at room temperature and which can be decomposed from the gas phase, that is to say are suitable for the various methods of gas-phase deposition.

It has now been found that organometallic compounds of aluminum, gallium and indium which are intramolecularly stabilized are outstandingly suitable for gas-phase deposition.

A few intramolecularly stabilized compounds of this type are described, for example, in German Offenlegungsschrift 3,631,469. This application describes, however, novel organometallic compounds having an intramolecular stabilization via a nitrogen, phosphorus, arsenic or antimony atom, or also having an intramolecular stabilization via fluorine atoms. All these intramolecularly stabilized compounds have a high stability toward air and oxygen, and they are therefore simple to handle and are outstandingly suitable for gas-phase deposition.

The invention consequently relates to organometallic compounds of the formula I:

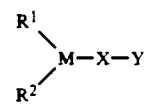

wherein

M denotes aluminum, indium or gallium,

Y denotes —NR$^3$R$^4$, —PR$^3$R$^4$, —AsR$^3$R$^4$, —SbR$^3$R$^4$, —F or a perfluorinated alkyl group containing 1-7 carbon atoms, X denotes, if Y=—F or a perfluorinated alkyl group containing 1-7 carbon atoms:

—(CHR$^5$)$_n$— where n=1, 2, 3, 4 or 5, o—(CH$_2$)$_p$—C$_6$H$_4$—(CH$_2$)$_q$—, 1,2—(CH$_2$)$_p$—C$_6$H$_{10}$—(CH$_2$)$_q$—, 1,2—(CH$_2$)$_p$—C$_6$H$_8$—(CH$_2$)$_q$—, 1,2—(CH$_2$)$_p$—C$_6$H$_6$—(CH$_2$)$_q$—, 1,2—(CH$_2$)$_p$—C$_5$H$_8$—(CH$_2$)$_q$—, 1,2—(CH$_2$)$_p$—C$_5$H$_6$—(CH$_2$)$_q$—, 1,2—(CH$_2$)$_p$—C$_5$H$_4$—(CH$_2$)$_q$—, 1,2—(CH$_2$)$_p$—C$_4$H$_6$—(CH$_2$)$_q$—, or a single bond, or if Y=—NR$^3$R$^4$, —PR$^3$R$^4$, —AsR$^4$R$^4$ or —SbR$^3$R$^4$:

o—C$_6$H$_4$—, 1,2—C$_6$H$_{10}$—, o—(CH$_2$)$_r$—C$_6$H$_4$—(CH$_2$)$_s$—, 1,2—(CH$_2$)$_r$—C$_6$H$_{10}$—(CH$_2$)$_s$—, 1,2—(CH$_2$)$_p$—C$_6$H$_8$—(CH$_2$)$_q$—, 1,2—(CH$_2$)$_p$—C$_6$H$_6$—(CH$_2$)$_q$—, 1,2—(CH$_2$)$_p$—C$_5$H$_8$—(CH$_2$)$_q$—, 1,2—(CH$_2$)$_p$—C$_5$H$_6$—(CH$_2$)$_q$—, 1,2—(CH$_2$)$_p$—C$_5$H$_4$—(CH$_2$)$_q$— or 1,2—(CH$_2$)$_p$—C$_4$H$_6$—(CH$_2$)$_q$—, r and s in each case denote, independently of each other, 1, 2 or 3, p and q in each case denote, independently of each other, 0, 1, 2 or 3, R$^1$, R$^2$, R$^3$ and R$^4$ in each case denote, independently of each other, an alkyl group or alkenyl group containing up to 8 carbon atoms, it being possible for these groups to be partially or completely fluorinated, a cycloalkyl group or cycloalkenyl group containing 3-8 carbon atoms or a phenyl group, and $R^5$ in each case denotes H or an alkyl group containing 1–4 carbon atoms, which may also be partially or completely fluorinated.

The invention further relates to the use of the compounds of the formula I for gas-phase deposition and also to a process for producing thin films or epitaxial layers by gas-phase deposition of the metal or of a III-V combination from organometallic compounds in which the compounds of the formula I are used as organometallic substances.

The compounds of the formula I are intramolecularly stabilized by electron transfer from the nitrogen, phosphorus, arsenic, antimony or fluorine atom to the electron-deficient III B element. They therefore have a high stability toward air and oxygen. They are no longer spontaneously ignitable and are consequently simple to handle. In the gas phase, however, the compounds according to the invention can easily be decomposed to deposit the metal. Since the compounds of the formula I contain stable and readily detachable departing groups, a lower incorporation of carbon results, and this has considerable advantages for the quality of the final products.

In formula I, M denotes aluminum (Al), gallium (Ga) or indium (In), preferably Ga or In.

Y preferably denotes F or a perfluorinated alkyl group containing 1–7 carbon atoms and accordingly preferably denotes trifluoromethyl, pentafluoroethyl, heptafluoropropyl or nonafluorobutyl, undecafluoropentyl, tridecafluorohexyl or pentadecafluoroheptyl.

Furthermore, Y preferably represents an $-NR^3R^4$ group, and furthermore also preferably a $-PR^3R^4$ or $-AsR^3R^4$ group.

Subformula Ia comprises the compounds which contain F or a perfluorinated alkyl group. Those compounds:

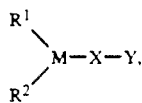
Ia wherein

M denotes Al, In or Ga,

Y denotes F, trifluoromethyl, pentafluoroethyl, heptafluoropropyl, nonafluorobutyl, undecafluoropentyl, tridecafluorohexyl or pentadecafluoroheptyl, X denotes —$(CHR^5)$ where n=1, 2, 3, 4, or 5, o—$(CH_2)_p$—$C_6H_4$—$(CH_2)_q$—, 1,2—$(CH_2)_p$—$C_6H_{10}$—$(CH_2)_q$—, 1,2—$(CH_2)_p$—$C_6H_8$—$(CH_2)_q$—, 1,2—$(CH_2)_p$—$C_6H_6$—$(CH_2)_q$—, 1,2—$(CH_2)_p$—$C_5H_8$—$(CH_2)_q$—, 1,2—$(CH_2)_p$—$C_5H_6$—$(CH_2)_q$—, 1,2—$(CH_2)_p$—$C_5H_4$—$(CH_2)_q$—, 1,2—$(CH_2)_p$—$C_4H_6$—$(CH_2)_q$—, or a single bond, p and q in each case denote, independently of each other, 0, 1, 2 or 3, $R^1$ and $R^2$ in each case denote, independently of each other, an alkyl group or alkenyl group containing up to 8 carbon atoms, it being possible for these groups to be partially or completely fluorinated, a cycloalkyl group or cycloalkenyl group containing 3–8 carbon atoms or a phenyl group, and $R^5$ in each case denotes H or an alkyl group containing 1–4 carbon atoms which may also be partially or completely fluorinated, are particularly preferred.

Those compounds of the subformula Ib are further preferred which contain as Y an $-N^3R^4$, $-PR^3R^4$, $-AsR^3R^4$ or $-SbR^3R^4$ group:

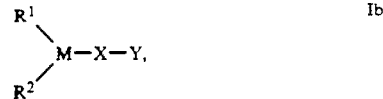
Ib wherein

M denotes Al, In or Ga,

Y denotes $-NR^3R^4$, $-PR^3R^4$, $-AsR^3R^4$ or $-SbR^3R^4$,

X denotes o—$C_6H_4$—, 1,2—$C_6H_{10}$—, o—$(CH_2)_r$—$C_6H_4$—$(CH_2)_s$—, 1,2—$(CH_2)_r$—$C_6H_{10}$—$(CH_2)_s$—, 1,2—$(CH_2)_p$—$C_6H_8$—$(CH_2)_q$—, 1,2—$(CH_2)_p$—$C_6H_6$—$(CH_2)_q$—, 1,2—$(CH_2)_p$—$C_5H_8$—$(CH_2)_q$—, 1,2—$(CH_2)_p$—$C_5H_6$—$(CH_2)_q$—, 1,2—$(CH_2)_p$—$C_5H_4$—$(CH_2)_q$— or 1,2—$(CH_2)_p$—$C_4H_6$—$(CH_2)_q$—, r and s in each case denote, independently of each other, 1, 2 or 3, p and q in each case denote, independently of each other, 0, 1, 2 or 3 and $R^1$, $R^2$, $R^3$ and $R^4$ in each case denote, independently of each other, an alkyl group or alkenyl group containing up to 8 carbon atoms, it being possible for these groups to be partially or completely fluorinated, a cycloalkyl group or cycloalkenyl group containing 3–8 carbon atoms or a phenyl group.

Among the compounds of the formula Ib, those are very particularly preferred in which Y denotes $-NR^3R^4$ or $-PR^3R^4$.

In formula I and Ia, X denotes $-(CHR^5)_n$, where n =1, 2, 3, 4 or 5, and n is preferably =3 or 4. $R^5$ represents either a hydrogen atom or an alkyl group, which may also be partially or completely fluorinated, containing up to 4 carbon atoms and accordingly preferably denotes methyl, ethyl, propyl, butyl, trifluoromethyl, tetrafluoroethyl, pentafluoroethyl or heptafluoropropyl. If $R^5$ is an alkyl group or partially or completely fluorinated alkyl group, preferably only in $R^5$ —$(CHR^5)_n$— is an alkyl group, the other $R^5$ groups possibly present then denoting H.

In formula I and Ib, X preferably denotes o—$C_6H_4$—, 1,2—$C_6H_{10}$— or also o—$(CH_2)_r$—$C_6H_4$—$(CH_2)_2$— or 1,2—$(CH_2)_r$—$C_6H_{10}$— $(CH_2)_s$—, where r and s in each case denote, independently of each other, 1, 2 or 3, preferably 1 or 2.

For X in formula Ia, the groups o—$(CH_2)_p$—$C_6H_4$—$(CH_2)_q$— and 1,2—$(CH_2)_p$—$C_6H_{10}$—$(CH_2)_q$, wherein p and q in each case denote, independently of each other, 0, 1, 2 or 3, preferably 0, 1 or 2, are also especially preferred.

Very particularly preferred for X in the subformula Ia is the single bond.

In the formulae I, Ia and Ib, X also further preferably denotes one of the following groupings (1)-(8) for —X—Y.

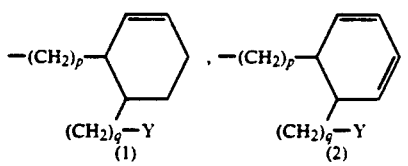
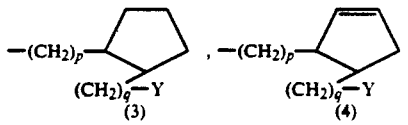
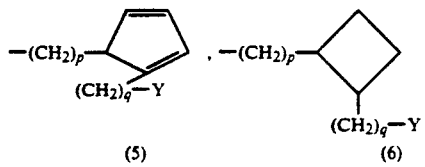
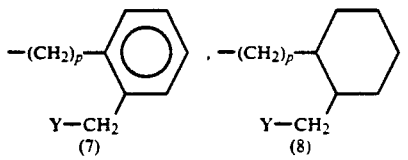

In the formulae (1), (2), (4) and (5), the double bonds may also be situated in all the other possible positions.

p and q in formula I preferably denote 1 or 2. In this connection, those compounds are preferred in which one of the groups p and q is 0 and the other denotes 1 or 2.

The radicals $R^1$, $R^2$, $R^3$ and $R^4$ in formula I may in each case denote a straight-chain or branched alkyl group containing 1-8 carbon atoms, preferably containing 1-4 carbon atoms. They are preferably straight-chain and accordingly preferably denote methyl, ethyl, propyl, butyl, furthermore also pentyl, hexyl, heptyl, octyl, isopropyl, sec-butyl, tert-butyl, 2-methylpentyl, 3-methylpentyl or 2-octyl. The alkyl radicals may be partially or even completely fluorinated and denote, for example, monofluoromethyl, trifluoromethyl, difluoroethyl, trifluoroethyl, pentafluoroethyl or trifluoropropyl.

If $R^1$, $R^2$, $R^3$ and/or $R^4$ denote a cycloalkyl or cycloalkenyl group containing 3-8 carbon atoms, they preferably denote cyclopropyl, cyclobutyl, cyclopentyl, cyclopentenyl, cyclohexyl, cyclohexenyl, cyclohexadienyl, cycloheptyl, cycloheptenyl, cycloheptadienyl, cyclooctyl, cyclooctenyl, cyclooctadienyl, cyclooctatrienyl or cyclooctatetraenyl.

Preferably, $R^1$, $R^2$, $R^3$ and/or $R^4$ also represent alkenyl groups containing 3-8 carbon atoms, preferably 3-5 carbon atoms. They accordingly preferably denote propenyl, butenyl, pentenyl, and furthermore hexenyl, heptenyl or octenyl.

Compounds of the formula I are furthermore preferred wherein $R^1$, $R^2$, $R^3$ and/or $R^4$ denote a phenyl group. Said phenyl group may also be present in substituted form. Since these substituents have no essential influence on the intended application, all those substituents are allowed which do not have any disturbing influence on the decomposition reaction.

The compounds of the formula Ia wherein Y denotes a perfluorinated alkyl group and $R^1$ and $R^2$ also denote alkyl groups which are partially or even completely fluorinated are also particularly preferred.

The following compounds of the formulae 7-27 represent a smaller group of particularly preferred compounds of the formula I:

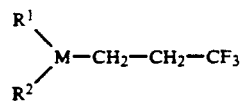
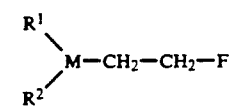
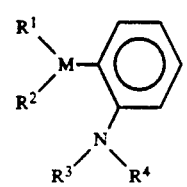
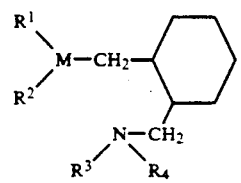
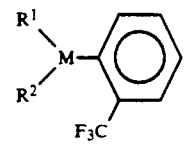
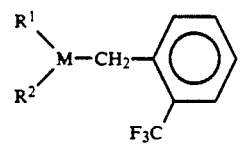
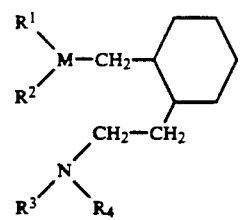
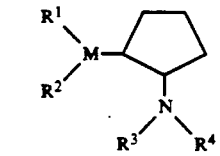
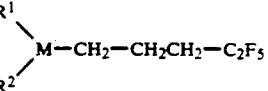

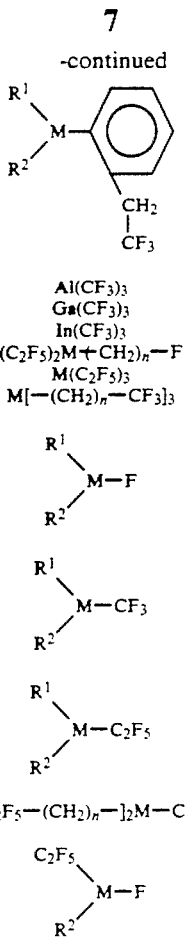

-continued

16

Al(CF$_3$)$_3$   17
Ga(CF$_3$)$_3$   18
In(CF$_3$)$_3$   19
(C$_2$F$_5$)$_2$M—(CH$_2$)$_n$—F   20
M(C$_2$F$_5$)$_3$   21
M[—(CH$_2$)$_n$—CF$_3$]$_3$   22

23

24

25

[C$_2$F$_5$—(CH$_2$)$_n$—]$_2$M—CF$_3$   26

27

The compounds of the formulae I, Ia and Ib are outstandingly suitable for the MOCVD epitaxy or MOCVD method since they decompose at elevated temperatures to release the corresponding metal. They are also suitable for the other methods of gas-phase deposition such as photo-MOVP, laser CVD or MOMS.

The compounds of the formulae I, Ia and Ib are prepared by methods known per se, such as are described in the literature (for example, G. Bähr, P. Burbar, Methoden der organischen Chemie [Methods of organic chemistry], volume XIII/4, Georg Thieme Verlag, Stuttgart (1970)) and, to be specific, under reaction conditions which are known and suitable for the reactions mentioned. At the same time, use may also be made of variants which are known per se and are not mentioned here in any detail.

Thus, compounds of the formulae I, Ia and Ib can be prepared, for example, by reacting metal alkyl chlorides with an alkali-metal organyl of the corresponding Lewis base or a Grignard compound in an inert solvent.

The reactions are preferably carried out in inert solvents. In this connection, all those solvents which do not disturb the reaction and do not interfere with the course of the reaction are suitable as solvents. The reaction temperatures essentially correspond to those which are known from the literature for the preparation of similar compounds.

In the process according to the invention for producing thin films or epitaxial layers on any desired substrates, the intramolecularly stabilized, organometallic compounds of the formula I are used as starting compounds in the gas-phase deposition processes, known per se, of organometallic compounds.

In the process according to the invention, to produce compound semiconductors, and optical and optoelectronic components, one or more compounds, which are gaseous under the reaction conditions used, of arsenic, antimony or phosphorus, for example AsH$_3$, As(CH$_3$)$_3$, PH$_3$ or SbH$_3$ are added during the deposition process in the decomposition chamber. A further variant of the process according to the invention is to add dopants additionally to the organometallic compounds of the formula I according to the invention during the deposition process. In this connection, volatile organometallic compounds of iron, magnesium, zinc or chromium are used as dopants. Preferred compounds in this connection are considered to be, for example, Zn(CH$_3$)$_2$, Mg(CH$_3$)$_2$ or Fe(C$_5$H$_5$)$_2$.

It is further possible to add the compounds of the formula I as dopants during the deposition process of other organometallic compounds.

The layers produced by the processes according to the invention can be used to produce electronic and optoelectronic circuit elements, compound semiconductors or lasers.

Since only approximately 1–10% of the free metal alkyls used can be deposited as epitaxial layer on the substrate for thermodynamic reasons in the epitaxial systems at present in use, the destruction of the excess metal alkyls, which cannot be recovered owing to their extreme sensitivity, represents a considerable problem. The compounds of the formula I according to the invention, on the other hand, open up new possibilities for the safe destruction or for the recovery of the valuable III B compounds owing to their high stability.

The following examples are intended to illustrate the invention in more detail. Temperatures are always specified in degrees characterized in that Celsius. Mp. denotes melting point and Bp. denotes boiling point

EXAMPLE 1

2.92 g (20 mmol) of trifluoromethylbenzene and 13.3 ml (1.5 N = 20 mmol) of n-butyllithium (in hexane) are heated under reflux in an ether/hexane solution (50 ml/25 ml) for approximately 8 hours. The mixture is then cooled to −40° and 1.62 g (12 mmol) of dimethylgallium chloride in 30 ml of hexane are added.

Precipitated lithium chloride is filtered off, the solvent is evaporated off and the residue is sublimed in vacuo. o-Trifluoromethylphenyldimethylgallium is obtained as a white solid, Mp. 32°.

The following are prepared in an analogous manner:
o-Trifluoromethylphenyldiethylgallium
o-Trifluoromethylphenyldipropylgallium
o-Trifluoromethylphenyldibutylgallium
o-Trifluoromethylphenyldimethylaluminum
o-Trifluoromethylphenyldiethylaluminum
o-Trifluoromethylphenyldipropylaluminum
o-Trifluoromethylphenyldiisobutylaluminum
o-Trifluoromethylphenyldimethylindium
o-Trifluoromethylphenyldiethylindium
o-Trifluoromethylphenyldiisopropylindium
o-Trifluoromethylphenyldibutvlindium
3,3,3-Trifluoropropyldimethylgallium
3,3,3-Trifluoropropyldiethylgallium
3,3,3-Trifluoropropylmethylethylgallium
3,3,3-Trifluoropropyldipropylgallium
3,3,3-Trifluoropropyldi-sec-butylgallium
3,3,3-Trifluoropropyldipentylgallium 3,3,3-Trifluoropropyldimethylaluminum
3,3,3-Trifluoropropyldipropylaluminum
3,3,3-Trifluoropropyldiethylindium
3,3,3-Trifluoropropyldiisopropylindium
3-Monofluoropropyldimethylgallium
3-Monofluoropropyldimethylaluminum
3-Monofluoropropyldimethylindium
3-Monofluoropropyldiethylgallium
3-Monofluoroprop-vldiethylaluminum
3-Monofluoropropyldiethylindium
2-Monofluoroethyldimethylgallium
2-Monofluoroethyldiethylgallium
2-Monofluoroethyldipropylgallium
2-Monofluoroethyldimethylaluminum
2-Monofluoroethyldiethylaluminum
2-Monofluoroethyldi-tert-butylaluminum
2-Monofluoroethyldiethylindium
2-Monofluoroethyldipentylindium

EXAMPLE 2

13.81 g (69 mmol) of bromodimethylaniline in 100 ml of ether are added to 1.23 g (177 mmol) of lithium in 60 ml of ether and stirring is carried out for 12 hours at 20°. Then heating is carried out for 2 hours to boiling point. After cooling, the solvent is removed in vacuo, hexane is added and the LiCl is filtered off. On cooling to −30°, the corresponding Li compound crystallizes out, and is isolated and dried.

4.6 g (34 mmol) of dimethylgallium chloride in 80 ml of pentane are then added at −40° to a suspension of 4.8 g (37.8 mmol) of this Li compound in pentane. The mixture is then stirred for 12 hours at room temperature and heated for a further 2 hours under reflux. The LiCl is filtered off, the solvent is distilled off in vacuo, and the residue has added pentane/toluene (20/1) to it and is cooled to −30°. During this process, o-dimethylaminophenyldimethylgallium crystallizes out which, after isolation, has a melting point of 104°.

The following are prepared in an analogous manner:
o-Dimethylaminophenyldiethylgallium
o-Dimethylaminophenyldipropylgallium
o-Dimethylaminophenyldibutylgallium
o-Dimethylaminophenyldimethylindium
o-Dimethylaminophenyldiethylindium
o-Dimethylaminophenyldiisopropylindium
o-Dimethylaminophenyldibutylindium
o-Dimethylaminophenyldimethylaluminum
o-Dimethylaminophenyldiethylaluminum
o-Dimethylaminophenyldipropylaluminum
o-Dimethylaminophenyldi-tert-butylaluminum
o-Dimethylaminophenyldipentylaluminum
o-Diethylaminophenyldimethylgallium
o-Diethylaminophenyldiethylaluminum
o-Diethylaminophenyldipropylindium
o-Dipropylaminophenyldimethylindium
o-Dipropylaminophenyldiethylgallium
o-Dipropylaminophenyldiisopropylaluminum
o-Dimethylaminomethylbenzyldimethylaluminum
o-Dimethylaminomethylbenz-vldiethylgallium
o-Dimethylaminomethylbenzyldipropylindium
1,2-Diethylaminomethylcyclohexylmethyldimethylgallium
1,2-Diethylaminomethylcyclohexylmethyldiethylgalliun
1,2-Diethylaminomethylcyclohexylmethyldiethylaluminum
1,2-Diethylaminomethylcyclohexylmethyldipropylaluminum
1,2-Diethylaminomethylcyclohexylmethyldibutylindium
1,2-Diethylaminomethylcyclohexylmethyldimethylindium
1,2-Dimethylaminomethylcyclopentyldimethylgallium
1,2-Dimethylaminomethylcyclopentyldiethylindium
1,2-Dimethylaminomethylcyclopentyldipropylaluminum

EXAMPLE 3

5.25 g (22 mmol) of o-trifluoromethylbenzyl bromide in 10 ml of ether/hexane are added at −50° to a mixture of 45 ml of ether/hexane (2:1) and 14.7 ml (1.5N =22 mmol) of n-butyllithium. After stirring for 15 minutes, 2.1 g (16 mmol) of dimethylgallium chloride in 20 ml of hexane are added. Then the reaction mixture is allowed to come to room temperature, it is stirred for 24 hours, and the LiCl is filtered off and the solvent removed. After sublimation in vacuo, o-trifluoromethylbenzyldimethylgallium is obtained with a Mp. 35°-38°.

The following are prepared in an analogous manner:
o-Trifluoromethylbenzyldiethylgallium
o-Trifluoromethylbenzyldipropylgallium
o-Trifluoromethylbenzyldibutylgallium
o-Trifluoromethylbenzyldimethylaluminum
o-Trifluoromethylbenzyldiethylaluminum
o-Trifluoromethylbenzyldipropylaluminum
o-Trifluoromethylbenzyldibutylaluminum
o-Trifluoromethylbenzyldipentylaluminum
o-Trifluoromethylbenzylethylpropylaluminum
o-Trifluoromethylbenzyldimethylindium
o-Trifluoromethylbenzyldiethylindium
o-Trifluoromethylbenzyldiisopropylindium
o-(2,2,2-Trifluoroethyl)benzyldimethylgallium
o-(2,2,2-Trifluoroethyl)benzyldiethylgallium
o-(2,2,2-Trifluoroethyl)benzyldiethylaluminum
o-(2,2,2-Trifluoroethyl)benzylmethylethylaluminum
o-(2,2,2-Trifluoroethyl)benzyldipropylindium
o-(2,2,2-Trifluoroethyl)benzyldimethylindium
o-(2-Monofluoroethyl)benzyldiethylgallium
o-(2-Monofluoroethyl)benzyldimethylindium
o-(2-Monofluoroethyl)benzyldipentylaluminum
o-(2-Monofluoroethyl)phenyldimethylgallium
o-(2-Monofluoroethyl)phenyldiisopropylaluminum
o-(2-Monofluoroethyl)phenyldiethylindium
o-(3-Monofluoropropyl)phenyldimethylgallium
o-(3-Monofluoropropyl)phenylmethylethylgallium
o-(3-Monofluoropropyl)phenyldiethylaluminum
o-(3-Monofluoropropyl)phenyldi-tert-butylaluminum
o-(3-Monofluoropropyl)phenyldipropylindium
o-(3-Monofluoropropyl)phenyldiethylindium
o-(3-Monofluoropropyl)benzyldimethylgallium
o-(3-Monofluoropropyl)benzyldimethylaluminum
o-(3-Monofluoropropyl)benzyldimethylindium
o-(3-Monofluoropropyl)benzyldiethylindium
o-(3-Monofluoropropyl)benzyldiethylaluminum
o-(3-Monofluoropropyl)benzyldipropylgallium
o-(3-Monofluoropropyl)benzyldiisopropylgallium
o-(3-Monofluoropropyl)benzyldibutylaluminum

EXAMPLE 4

1.95 g (8.48 mmol) of $(CF_3)_2$ Cd . DME (DME=dimethoxyethane) in 20 ml of benzene are added slowly at −70° C. to a mixture of 20 ml of benzene and 1 g (5.66 mmol) of $GaCl_3$. After heating to room temperature, tris(trifluoromethyl)gallium is obtained by fractional distillation.

The following are prepared in an analogous manner:
tris(trifluoromethyl)indium
tris(pentafluoroethyl)gallium
tris(pentafluoroethyl)indium
tris(heptafluoropropyl)gallium
tris(heptafluoropropyl)indium

We claim:

1. Organometallic compounds of the formula I:

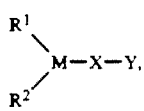

wherein

M denotes aluminum, indium or gallium,

Y denotes $-NR^3R^4$, $-PR^3R^4$, $-AsR^3R^4$, $-SbR^3R^4$, $-F$ or a perfluorinated alkyl group containing 1-7 carbon atoms.

X denotes, if $Y = -F$ or a perfluorinated alkyl group containing 1-7 carbon atoms:
$-(CHR^5)_n$ where $n = 1, 2, 3, 4$ or 5,
$o-(CH_2)_p-C_6H_4-(CH_2)_q-$,
$1,2-(CH_2)_p-C_6H_{10}-(CH_2)_q-$,
$1,2-(CH_2)_p-C_6H_8-(CH_2)_q-$,
$1,2-(CH_2)_p-C_6H_6-(CH_2)_q-$,
$1,2-(CH_2)_p-C_5H_8-(CH_2)_q-$,
$1,2-(CH_2)_p-C_5H_6-(CH_2)_q-$,
$1,2-(CH_2)_p-C_5H_4-(CH_2)_q-$,
$1,2-(CH_2)_p-C_4H_6-(CH_2)_q-$, or if
$Y = -NR^3R^4$, $-PR^3R^4$, $-AsR^3R^4$ or $-SbR^3R^4$:
$o-C_6H_4-$,
$1,2-C_6H_{10}-$,
$o-(CH_2)_r-C_6H_4-(CH_2)_s-$,
$1,2-(CH_2)_r-C_6H_{10}-(CH_2)_s-$,
$1,2-(CH_2)_p-C_6H_8-(CH_2)_q-$,
$1,2-(CH_2)_p-C_6H_6-(CH_2)_q-$,
$1,2-(CH_2)_p-C_5H_8-(CH_2)_q-$,
$1,2-(CH_2)_p-C_5H_6-(CH_2)_q-$,
$1,2-(CH_2)_p-C_5H_4-(CH_2)_q-$ or
$1,2-(CH_2)_p-C_4H_6-(CH_2)_q-$, r and s in each case denote, independently of each other, 1, 2 or 3, p and q in each case denote, independently of each other, 0, 1, 2 or 3, $R^1$, $R^2$, $R^3$ and $R^4$ in each case denote, independently of each other, an alkyl group or alkenyl group containing up to 8 carbon atoms, it being possible for these groups to be partially or completely fluorinated, a cycloalkyl group or cycloalkenyl group containing 3-8 carbon atoms or a phenyl group, and $R^5$ in each case denotes H or an alkyl group containing 1-4 carbon atoms, which may also be partially or completely fluorinated.

2. The use of the organometallic compounds of the formula I according to claim 1 for the gas-phase deposition of the metal of the main group III or of a III-V combination on substrates.

3. The use of the organometallic compounds of the formula I according to claim 1 for the deposition of epitaxial layers.

4. Process for the production of thin films on substrates by gas-phase deposition of the metal of the main group III or of a III-V combination from organometallic compounds, characterized in that the compounds of the formula I according to claim 1 are used as organometallic compounds.

5. Process according to claim 4, characterized in that one or more compounds of arsenic, antimony or phosphorus which are gaseous under the reaction conditions used are supplied for the production of compound semiconductors, and of optical and opto-electronic components during the deposition process.

6. Process according to claim 4, characterized in that dopants are added additionally to the organometallic compounds of the formula I during the deposition process.

7. Process according to claim 4, characterized in that the compounds of the formula I are added as dopants during the deposition process of other organometallic compounds.

* * * * *